United States Patent [19]

Koeniger et al.

[11] Patent Number: 5,882,663
[45] Date of Patent: Mar. 16, 1999

[54] TOPICAL PAIN-RELIEVING PREPARATION CONTAINING $C_{12}$ TO $C_{18}$ ISOPARAFFINS

[76] Inventors: Erich A. Koeniger, 5600 Bridget St., Metairie, La. 70003; Drahoslay Lim, 7110 Dennison Pl., San Diego, Calif. 92122

[21] Appl. No.: 867,673

[22] Filed: Jun. 2, 1997

Related U.S. Application Data

[63] Continuation of Ser. No. 546,326, Oct. 20, 1995, abandoned.

[51] Int. Cl.$^6$ .......................... A61K 31/01; A61K 9/107; A61K 31/60
[52] U.S. Cl. .................. 514/762; 424/78.02; 424/70.11; 424/70.1; 424/195.1; 514/937; 514/944; 514/945; 514/947; 514/969; 514/817; 514/887; 514/1
[58] Field of Search ................................ 424/401, 78.02, 424/70.11, 70.1, 484, 450, 195.1; 514/937, 944, 945, 947, 969, 817, 887, 762, 1

[56] References Cited

U.S. PATENT DOCUMENTS

| | | |
|---|---|---|
| 4,353,896 | 10/1982 | Levy . |
| 4,844,902 | 7/1989 | Grohe . |
| 5,011,681 | 4/1991 | Ciotti et al. . |
| 5,236,697 | 8/1993 | Schrauzer . |
| 5,293,885 | 3/1994 | Darkwa et al. . |

OTHER PUBLICATIONS

Goldenberg, R.L. (1995). Drug & Cosmetic Industry vol. 156, p. 68.

Fox, C. (1992). Cosmetics and Toiletries, vol. 107, p. 69.

*Primary Examiner*—Raj Bawa
*Attorney, Agent, or Firm*—Morgan & Finnegan, L.L.P.

[57] ABSTRACT

A method for providing pain relief includes topically applying to skin tissue an effective amount of higher homologs of isoparaffins, ranging from about $C_{12}$ to $C_{18}$. Compositions of the present invention include, with the isoparaffins in a mixture, at least one from the group consisting of salicylate, capsaicin, camphor, and menthol. Other constituents may be added for form creams or lotions.

8 Claims, No Drawings

TOPICAL PAIN-RELIEVING PREPARATION CONTAINING $C_{12}$ TO $C_{18}$ ISOPARAFFINS

This is a continuation of application Ser. No. 08/546,326, filed on Oct. 20, 1995, now abandoned.

BACKGROUND OF THE INVENTION

1. Field of the Invention

This invention relates to topical medicinal preparations and methods for their use, and in particular, to topical pain relief compositions which contain an alkane-based active ingredient.

2. Description of the Related Art

Pain relief of minor aches or soreness caused by injury to muscles, tendons, or any other such affliction which results in either pain or stiffness of joints and muscles has been addressed in the past with topical applications. In particular, it is known that minor aches such as those noted above can be temporarily relieved by non-prescription topical lotions and creams.

Known topical lotions and creams have been based on either salicylates, capsaicin, menthol, camphor or combinations thereof. It is understood that these compositions function via mechanisms which act predominantly upon the top epidermal layers of skin and sooth the nerve terminals which are located in the application area.

Although the known preparations provide various levels of pain relief, the use thereof has been associated with several problems. Namely, due to the nature of the active ingredients, the products are not without potential for skin irritation, especially with respect to sensitive areas of the body. Of the active components mentioned above, salicylates and capsaicin are the most powerful, but they are also classified as toxic irritants. Therefor, they can only be used in relatively low concentrations.

Additionally, most the known preparations contain an undiscriminating odor which cannot be easily masked. This odor is offensive to many and therefore some individuals in need of such treatment choose not to apply these compositions which are characterized with such a strong odor.

Finally, most of the above-mentioned preparations leave the skin greasy for a considerable time which may cause staining of clothing.

SUMMARY OF THE INVENTION

We have found by the study of biomedical properties of a series of higher isoparaffins, that their homologs, ranging from about $C_{12}$ to $C_{18}$, when applied topically on the skin in the proper regimen and in sufficient concentration, exhibit an unexpectedly good pain relieving potency without skin irritation or perceptible odor. Also, they do not form a long-lasting greasy film on the skin. Because purified higher homologs of isoparaffins are generally non-toxic and less irritating to the skin than most other organic compounds, mixtures thereof can be applied topically in a proper regimen with substantially no adverse effects.

Although various isoalkanes have been used in cosmetic formulations as solvents, emollients or inert diluents, it has heretofore gone unrecognized that higher isoparaffins outlined above can impart a high level of pain relief to muscles, skin and the like when applied topically in sufficient concentration.

Specific isoparaffin mixtures are readily obtained by fractional distillation from a broader range of purified technical product. Depending on the temperatures at which the fractions are collected and the efficiency of the separations, either broader or narrower mixtures of homolog mixtures may be prepared. Optimization of the fractional distillation process to obtain a specific homolog or a specific homolog mixture is considered to be within the skill of the ordinary artisan.

In this regard, mixtures of the desired particular higher homologs or mixtures thereof according to the invention are readily available in the commercial market. These commercial isoparaffin mixtures are in general designated by the name of the most abundant homolog or homologs which are contained therein. Examples of such commercially available products include $C_9$–$C_{11}$ isoparaffins, $C_{11}$–$C_{13}$ isoparaffins, $C_{13}$–$C_{16}$ isoparaffins, $C_{20}$–$C_{40}$ isoparaffins, and similar products.

Lower isoparaffins up to about isoundecane are fairly volatile and therefore they are suitable only for use in products wherein evaporation of the components is desirable. Also, they do not have the same effect on the skin as higher homologs. Hence, the volatile lower isoalkanes would not be suitable for inclusion in the contemplated preparations.

However, homologs of isoparaffins from about isododecane $C_{12}$ to isohexadecane $C_{16}$ whose boiling points are well above 200° C., and as mentioned above, which are also well tolerated by the skin, can be effectively included in topical preparations without any substantial evaporation thereof in use. When isoparaffins in the range of $C_{12}$ to $C_{18}$, ($C_{13}$ to $C_{16}$ being most preferred), are applied topically to the skin, either undiluted or as the main or an active agent in a skin preparation, they exhibit the right balance of overall properties for a distinct and long lasting pain relieving effect without the undesirable side effects of the known preparations.

Besides the lasting pain relieving effect, the advantage of isoparaffins specified above is that they are readily and completely absorbed by the stratum corneum epidermal layer and as such, do not remain on the surface of the skin as a greasy layer which might stain clothing. Also, when properly applied, they do not cause irritation, dryness or any alteration of the skin's texture.

With respect to isoparaffin homologs with more than 18 carbon atoms, although these compounds still continue to be beneficial to some degree, their pain relieving effect begins to be weaker and the absorption by the stratum corneum proceeds slower than that of isoalkanes with the number of carbon atoms specified above.

For pain relieving purposes, the isoparaffins according to the present invention may be employed in the form of any known topical preparation which may include vehicles and adjuvants commonly known in the art. Such topical preparations typically consist of lotions or creams. The preferred content of $C_{12}$ to $C_{18}$ isoparaffins in the preparation may range from about 30% to 100%. Although concentrations below 30% may be employed, the pain relieving effect by isoparaffin as the only active ingredient will decrease. As will be described below, the pain relieving effect of diluted specified isoalkanes or of isoalkanes with more than the optimum number of carbon atoms can be increased by the addition of some of the prior art ingredients, however.

To maximize the emollient action of the isoparaffins, it is advantageous to include therewith, some content of light mineral oil, silicone, or other commonly employed emollient in the neighborhood of from about 2% by weight. Further, to ensure stability against oxidation, some quantity of one or more antioxidants such as vitamin E may also be included.

Higher isoparaffins of this invention are mild emollients. Advantageously, the lotions can be formulated with some additional suitable emollients not only to increase the emollient effect, but also to help prolong the pain relieving action without introduction of greasiness. Examples of such emollients are light mineral oil and dimethicone employed in amounts of about several percent or more. When isoparaffins are used in the form of a cream, these emollients do not need to be added because creams contain already larger amounts of emollients as the part of the cream-forming base. To ensure the stability against oxidation, a small quantity of one or more antioxidants such as vitamin E, propyl gallate and similar additives may be included.

In preparations, isoparaffins may be employed alone or in combination with any other active ingredient useful for topical relief. Such formulations exhibit a synergistic effect. In this regard, when used in combination with salicylates, it is possible to formulate the preparation with a lower amount of this ingredient, which decreases the strong odor of the salicylate and enhances the pain relief attained by that lower content of the salicylate alone.

Isoparaffins may also be employed with capsaicin. Although capsaicin is known to cause skin irritation, when used in combination with isoparaffins, the quantity of capsaicin can be substantially reduced for the same effect as with a higher content of capsaicin alone, thus allowing for a superior product. The combination of isoparaffins with the aforementioned known ingredients is especially useful for isoparaffins with more than about 18 carbon atoms which by themselves exhibit a weaker pain relieving effect.

The following nonlimiting examples are intended to demonstrate how to make and use the invention described above.

EXAMPLES

Example 1

A lotion was formed by mixing 96 percent isoparaffins $C_{13}$–$C_{16}$ containing as the main component isoparaffins $C_{14}$–$C_{15}$, 2 percent cosmetic quality light mineral oil and 2 percent dimethicone. The lotion was stabilized by the addition of 0.005 parts vitamin E. When applied to the skin, the lotion is absorbed in about 10 minutes. The pain relieving effect lasted from about 4 to 16 hours. The lotion provides the same effect and without any noticeable skin irritation when applied topically up to 3 times per day for a period of up to 4 days.

Example 2

A lotion was formed by mixing 35 percent isoparaffins as described in Example 1, 10 percent glycerol monostearate, 5 percent cetyl alcohol, 5 percent PEG-100 stearate, 0.02 percent propyl gallate and 0.01 percent capasaicin. The ingredients were stirred at 65° C. to form a uniform mixture. To this mixture was slowly added under stirring and heating 30 percent water. Stirring and heating was continued until the mixture became a thin dispersion. Heating was then discontinued, stirring was slowed down and continued until the temperature dropped to room temperature. The resulting cream has distinct emollient properties, is fully absorbed in about 30 minutes and is used whenever a stronger emollient effect is preferred. Its pain relieving properties are similar to those of undiluted isoparaffins due to the presence of small amount of capsaicin.

Example 3

A lotion was formed by admixing 94 percent isoparaffins as described in Example 1, 2 percent cosmetic quality light mineral oil, 4 percent dimethicone, 0.01 percent capasaicin and 0.005 percent vitamin E. The pain relieving effect of this lotion is of the same duration as in Example 1, but is stronger due to the presence of a small amount of capsaicin.

What is claimed is:

1. A method for providing pain relief consisting essentially of the step of topically applying to skin tissue a preparation having an effective amount of higher homologs of isoparaffins ranging from about $C_{12}$ to $C_{18}$, wherein the preparation has about 20 wt. % to about 100 wt. % of the $C_{12}$ to $C_{18}$ isoparaffin.

2. The method according to claim 1, wherein the applying step includes rubbing a lotion containing the isoparaffins onto the skin tissue.

3. The method according to claim 1, further comprising repeating the applying step up to three times per day for up to four days.

4. A method for providing pain relief consisting essentially of the step of topically applying to skin tissue a lotion composition having about 30 wt. % to about 100 wt. % of higher homologs of isoparaffins ranging from about $C_{12}$ to about $C_{18}$.

5. A method according to claim 4, wherein the lotion further has at least one other active ingredient active for topical pain relief.

6. A method according to claim 5, wherein the other active ingredient is a salicylate or capsaicin compound.

7. A method according to claim 4, wherein the lotion further has a stabilizing additive.

8. A method according to claim 4, wherein the lotion further has mineral oil.

* * * * *